United States Patent [19]
Conway

[11] Patent Number: 5,757,457
[45] Date of Patent: May 26, 1998

[54] REMOVABLE NOSEPIECE FOR A UNITARY LENS

[75] Inventor: Simon M. Conway, New York, N.Y.

[73] Assignee: Bausch & Lomb Incorporated, Rochester, N.Y.

[21] Appl. No.: 633,383

[22] Filed: Apr. 16, 1996

Related U.S. Application Data

[62] Division of Ser. No. 330,485, Oct. 28, 1994, abandoned.

[51] Int. Cl.⁶ .................................................. G02C 5/12
[52] U.S. Cl. .................................... 351/138; 351/136
[58] Field of Search ................................ 351/138, 137, 351/136, 41, 44

[56] References Cited

U.S. PATENT DOCUMENTS

| | | | |
|---|---|---|---|
| 2,397,243 | 3/1946 | Cooper | 88/41 |
| 2,423,539 | 7/1947 | Williams | 88/41 |
| 2,482,664 | 9/1949 | Gagnon | 88/41 |
| 2,534,655 | 12/1950 | Baratelli | 2/14 |
| 2,582,345 | 1/1952 | Moeller | 88/55 |
| 2,801,569 | 8/1957 | Ralph | 88/51 |
| 3,016,797 | 1/1962 | Liautaud | 88/43 |
| 3,345,121 | 10/1967 | De Angelis | 351/130 |
| 3,391,976 | 7/1968 | Lindblom | 351/130 |
| 3,476,468 | 11/1969 | Fortenberry | 351/130 |
| 3,584,939 | 6/1971 | Olson | 351/132 |
| 4,405,214 | 9/1983 | Bolle | 351/88 |
| 4,470,674 | 9/1984 | Piampiano | 351/136 |
| 4,704,015 | 11/1987 | Grendol | 351/138 |
| 4,707,089 | 11/1987 | Danloup | 351/138 |
| 4,951,322 | 8/1990 | Lin | 2/439 |
| 5,032,017 | 7/1991 | Bolle | 351/116 |
| 5,182,586 | 1/1993 | Bennato | 351/47 |
| 5,526,070 | 6/1996 | Simioni | 351/138 |

FOREIGN PATENT DOCUMENTS

| | | |
|---|---|---|
| 457706 | 6/1949 | Canada . |
| 78 06923 | 10/1979 | France . |
| 79 29983 | 7/1981 | France . |
| 3121877A1 | 12/1982 | Germany . |
| 2117919A | 10/1983 | United Kingdom . |

Primary Examiner—Hung X. Dang
Attorney, Agent, or Firm—Katherine McGuire; Craig E. Larson

[57] ABSTRACT

A unique unitary lens for eyewear includes right and left lens regions formed of substantially spherical portions. The lens provides improved aerodynamics, aesthetic appearance and eye protection for sport eyewear applications.

7 Claims, 4 Drawing Sheets

REMOVABLE NOSEPIECE FOR A UNITARY LENS

This is a divisional of application Ser. No. 08/330.485 filed on Oct. 28, 1994, now abandoned.

BACKGROUND OF THE INVENTION

The present invention relates to eyewear having a unitary lens with two substantially spherical lens regions. The unitary lens is designed to extend around the wearer's eyes throughout a wide range of vision, and to provide improved aerodynamics, aesthetic appearance and eye protection.

Additionally, the invention provides connecting members for connecting temples to a lens and a nosepiece that are suitable for use with the unitary lens.

Eyewear for sports sunglass applications is designed for use during sporting activities such as skiing, biking, speed skating, volleyball, and the like. It is desirable that these types of sunglasses intercept peripheral light, protect the eyes from impact, and offer a comfortable fit.

One type of wrap-around or shield-type eyewear that is currently marketed for sports sunglass applications is characterized by a unitary cylindrical or unitary spherical shaped lens made of a plastic material such as a polycarbonate. However, such sunglasses having a unitary cylindrical or spherical shaped lenses tend not to conform closely to the wearer's head. The geometry of these lenses is defined primarily by a single segment of a cylinder, or a single segment of a sphere, whereas typical anatomical head shapes are not cylindrical or spherical in shape, particularly across the face. The nonconformity between the lens shape and head and face shape is further complicated by the fact that head and face shapes vary greatly among individual persons. This mismatch may result in eyewear which does not closely and comfortably fit the head of the wearer, resulting in a sacrifice of comfort, aerodynamic shape and protection of the eyes.

Another type of eyewear for sports sunglass applications is disclosed in U.S. Pat. No. 4,741,611 (Burns). This eyewear has a unitary front, molded from a plastic material such as polycarbonate, having a pair of lenses connected by an integral bridge, and includes a separate nosepiece that wraps around the bridge. The lenses have toric inner and outer surfaces and provide a fairly large wrap depth. This eyewear is characterized as avoiding the "bug-eyed" appearance of related eyewear having a pair of spherical lenses connected by an integral bridge, such as disclosed in U.S. Pat. No. 3,526,449 (Bolle et al.).

However, in the sunglasses disclosed in U.S. Pat. Nos. 4,741,611 and 3,526,449, a wearer's vision may be blocked by the wrap-around nosepiece, or the bridge may tend to distort vision of the wearer. Further, although the sunglasses disclosed in U.S. Pat. No. 4,741,611 have a fairly large wrap depth laterally, protection from below or above the eyes is limited.

SUMMARY OF THE INVENTION

In a first embodiment, the invention relates to a unitary lens for eyewear comprising a top edge, a bottom edge, and first and second (right and left) lens regions, wherein the bottom edge has a central indentation between the lens regions. In one aspect, the outer surfaces of the lens regions are defined by respective first and second substantially spherical portions, wherein a linear horizontal distance between the centerpoint of the first substantially spherical portion and the centerpoint of the second substantially spherical portions is no more than 4.0 cm. In another aspect, the lens regions are characterized as having substantially spherical outer surfaces joined by a blended juncture.

The present invention is also directed to eyewear having the described unitary lens and which is particularly adapted for use during sports activities. The eyewear is specifically designed to closely fit the head and face of the wearer to improve peripheral vision, to enhance protection of the eyes, and to be aerodynamic in appearance and function. The lens of the invention conforms more closely to the front and the sides of the wearer's head, thereby maximizing the interception of peripheral light. Each lens portion of the unitary lens is relatively uniformly spaced from the eye at all angular ranges of vision, thereby providing improved peripheral vision and eliminating the annoyance of eyelashes contacting the lens surface, a common problem with improperly fit unitary cylindrical shaped lenses. In a preferred embodiment, the lens is tinted for sunglass eyewear applications.

According to other embodiments, the invention relates to eyewear employing unique connecting members for connecting temples to lenses, and a nosepiece suitable for use with the unitary lens. These features are adapted for interchangeable lenses and temples so that eyewear can be modified according to a desired use.

DETAILED DESCRIPTION OF PREFERRED EMBODIMENTS

Figure 2:
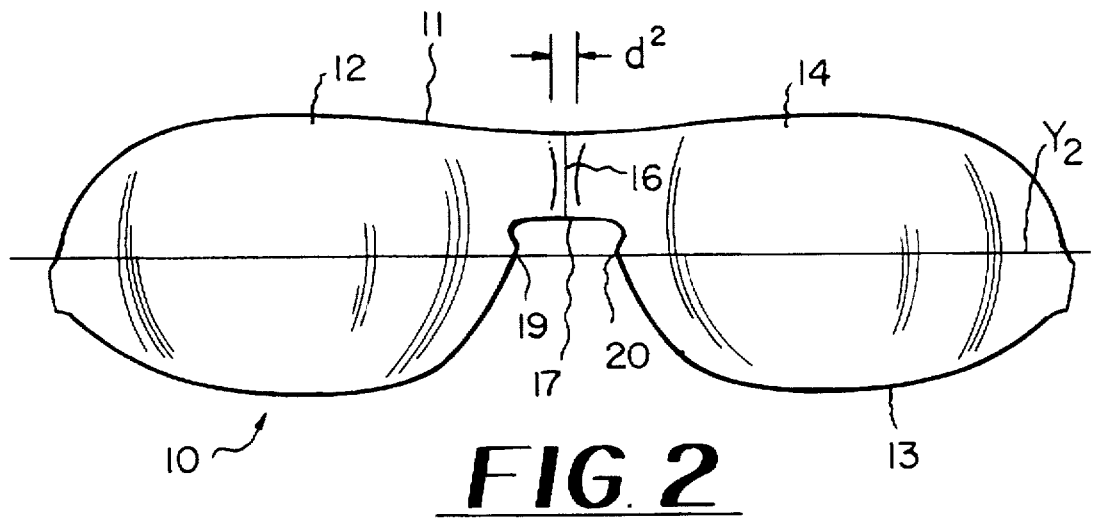
FIG. 2 is a front view of the lens shown in FIG. 1.
Figure 3:
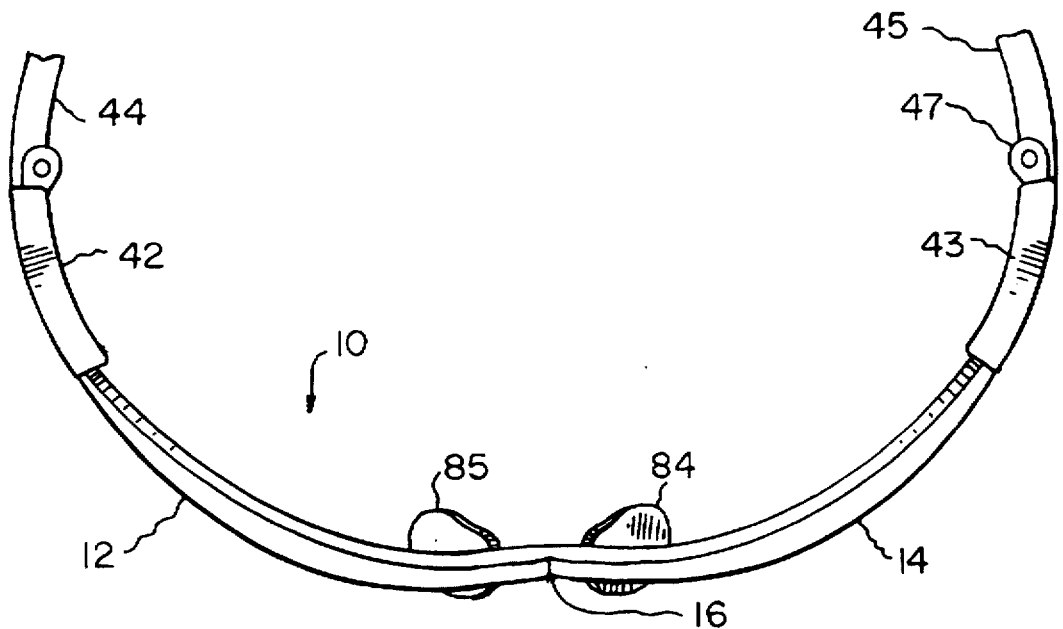
FIG. 3 is a top view of eyewear including a lens and connecting members of the invention, and partial temples.
Figure 4:
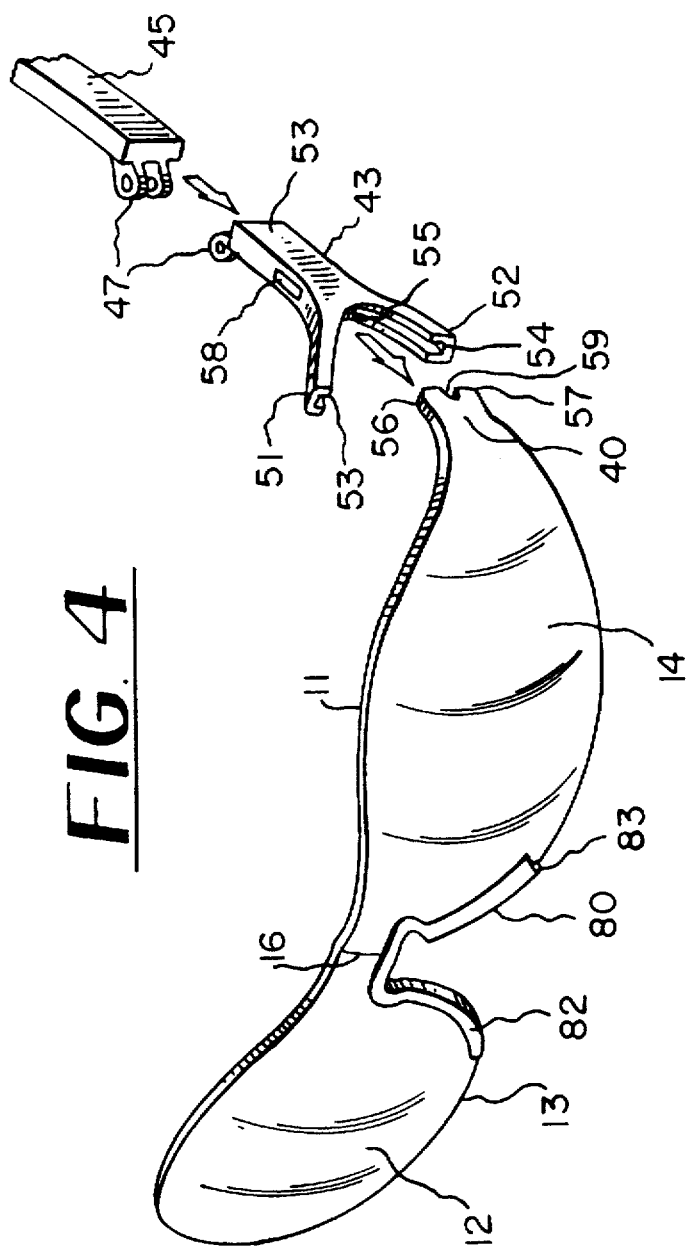
FIG. 4 is a partial, perspective, exploded view of the eyewear shown in FIG. 3.
Figure 5:
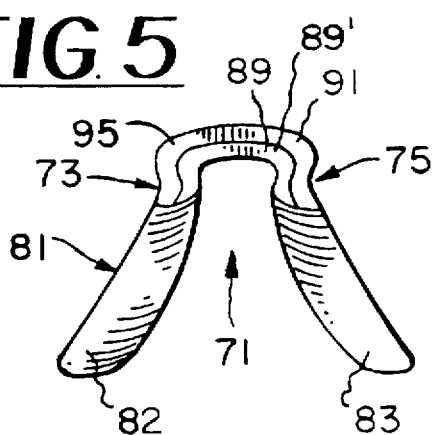
FIG. 5 is a front view of a nosepiece of the invention.
Figure 6:
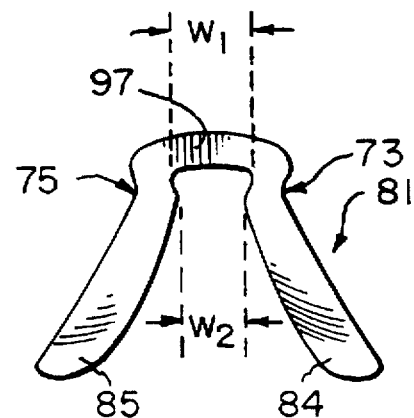
FIG. 6 is a back view of the nosepiece of FIG. 5.
Figure 7:
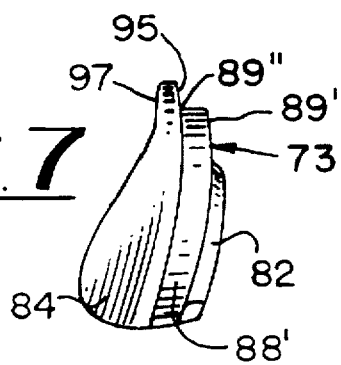
FIG. 7 is a side view of the nosepiece of FIG. 5.
Figure 8:
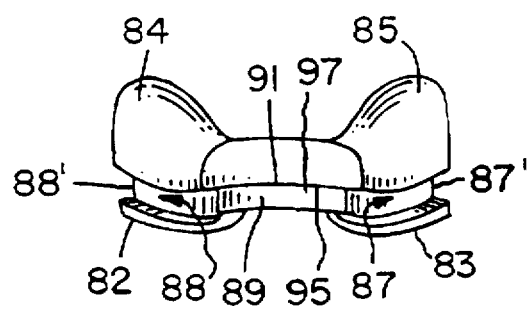
FIG. 8 is a top view of the nosepiece of FIG. 5.

As shown in FIGS. 1 to 4, unitary lens 10 has a first (or right) lens region 12 and a second (or left) lens region 14, unitary lens 10 being further defined by top edge 11 and bottom edge 13. Bottom edge 13 has an upwardly curved central indentation 17 between lens regions 12,14. Indentation 17 may be designed to fit directly over the bridge of the nose of the wearer, or to receive nosepiece 80 for placement on the bridge of the nose (as shown in FIG. 4).

Outer surfaces 2, 4 of respective lens regions 12, 14 are substantially spherical (i.e., a portion of a substantially spherical object). Preferably, the inner surfaces of lens regions 12, 14 are substantially spherical, also, so that the lens regions do not distort vision of a wearer (nor provide a power correction). It is preferred that outer surfaces 2,4 and inner surfaces are spherical. However, since these surfaces may deviate slightly from truly spherical portions without imparting noticeable distortion to a wearer's vision, the term "substantially spherical portion" and like terms is used to denote configurations with such minor deviations. (Hereinafter, description of the lens geometry will refer primarily to the preferred embodiment where these lens surfaces are spherical for purposes of clarity.)

In a first preferred aspect, outer surfaces 2,4 are defined by respective first and second substantially spherical portions, wherein the linear horizontal distance ($d^1$) between the centerpoints of these two portions is no more than 4.0 cm.

Figure 1:
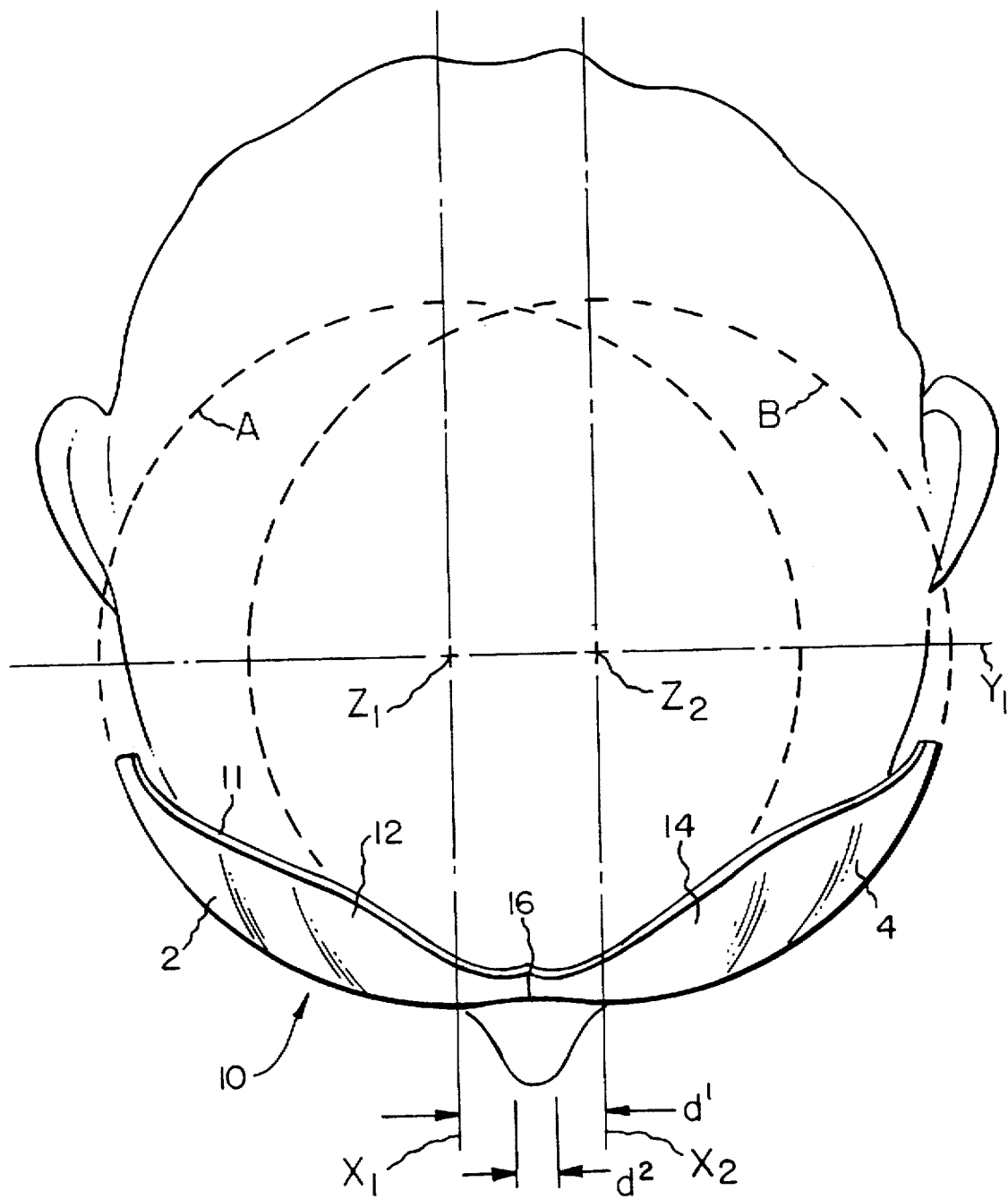
FIG. 1 is a top view of a lens made in accordance with a preferred embodiment of the present invention showing the relationship of the lens to a wearer's head.

More specifically, as best illustrated in the top view of FIG. 1, the centerpoint of imaginary sphere A (a portion of which forms outer surface 2 of lens region 12) is represented by point $Z_1$, lying at the intersection of vertical Plane $Y_1$, vertical Plane $X_1$, and horizontal Plane $Y_2$. Similarly, the centerpoint of imaginary sphere B (a portion of which forms outer surface 4 of lens region 14) is represented by point $Z_2$ which lies at the intersection of vertical Plane $Y_1$, horizontal Plane $X_9$, and horizontal plane $Y_2$. Plane $Y_1$ is an imaginary vertical plane which traverses the wearer's head between the temples as shown in FIG. 1, and Plane $Y_2$ is an imaginary horizontal plane which traverses the eye regions as shown in FIG. 2. Each of Planes $X_1$ and $X_2$ is an imaginary vertical plane that is substantially perpendicular to Plane $Y_1$ and extends from the front to the back of the wearer's head as shown in FIG. 1. The distance $d^1$ between Planes $X_1$ and $X_2$ (or the linear horizontal distance between centerpoints $Z_1$ and $Z_2$) is from about 0.1 to about 4.0 cm, preferably 1.0 to 3.0 cm, and more preferably from 2.0 to 3.0, especially about 2.5 cm.

It has been found that this geometry helps to ensure that lens regions 12, 14 fit closely over respective eye regions of the wearer without distorting or blocking vision of the wearer in the central portion of the lens. More specifically, the relatively narrow separation between $Z_1$ and $Z_2$ ensures a closer fit for a wider range of head and face shapes than has been available with conventional unitary lens designs having a single cylindrical or spherical shape across the face of the lens, while providing protection throughout the peripheral range of vision.

Preferably, the radius of curvature of outer surfaces 2,4 (i.e., the radius centered at centerpoints $Z_1$, $Z_2$) is from about 5 to about 7 cm, more preferably from about 5.5 to about 6.0 cm. The radius of curvature of the inner surfaces will be smaller than that of the outer surfaces, but the radius of curvature of the inner surfaces will also be within the same preferred ranges. The thickness of lens 10 may be uniform across the lens regions or may vary slightly (e.g., thicker at the center of lens 10 tapering to a thinner thickness towards the sides of lens 10), as long as the lens regions do not impart noticeable distortion to a wearer's vision. Generally, the thickness of lens 10 will be within the range of about 0.05 to about 0.5 cm.

In a second preferred aspect, outer surfaces 2,4 are joined by blended juncture 16 that is integral with surfaces 2,4. In other words, the transition between outer surfaces 2,4 has a minimal width and is designed to ensure further that lens regions 12, 14 provide the desired close fit without blocking or distorting vision at the central portion of lens 10.

It is preferred that juncture 16 (i.e., the transition area where the two substantially spherical portions forming lens regions 12 and 14 meet) has a linear horizontal width $d^2$ of 0.1 to 1.0 cm, preferably 0.4 to 0.8 cm. The exact configuration of blended juncture 16 is less critical than the configuration of the lens regions, but it is preferred that lens regions 12, 14 are integrally and smoothly blended into a unitary lens. For example, juncture 16 may be shaped as a portion of a torus, but other configurations are possible. (For comparison, for when $d^2$ is zero, the juncture between outer surfaces 2,4 would have the form of an arc.) Lens 10 is generally prepared from an optical plastic. A lens blank 90 (shown in FIG. 9) may be premolded using known injection molding or compression molding methods, whereafter a blended juncture 16 can be polished into blank 90 if desired. Thereafter, lens 10 of a desired shape can be cut from blank 90, for example, a lens having the configuration shown by the dashed lines in FIG. 9. An advantage of this process is that lenses having different shapes and sizes can be cut from the same standard blank. thermoplastic material such as those generally described above for lens 10. Alternatively, the connecting member can be made from a thermoplastic material such as polypropylene or an thermoplastic elastomer. Lens 10 can be transparent, or colored for sunglass applications using a variety of dyes as is known in the art. If desired, lens 10 can be coated with an optical coating (e.g., to enhance light at certain wavelength regions or to provide anti-reflection at the back surface of the lens), or with a scratch-resistance coating.

Lens 10 of the present invention may be attached to a frame member (not shown) using conventional techniques. As examples, lens 10 may be provided with a top frame member extending along only the upper edge of the lens, or a front frame member can extend around the periphery of lens 10. Temples can then be attached to the top or front frame members. Alternatively, temples can be attached directly to lens 10, without the use of a top or front frame member, using conventional techniques known in the art such as fasteners, adhesives, or locking interfit connections. It is also within the scope of the invention to attach a rear strap to the lens, or its frame members, as commonly used on ski goggles, to hold more firmly lens 10 in proper position on the head and face of the wearer.

FIGS. 3 to 4 illustrate one preferred embodiment for connecting temples to lens 10 that employs a unique connecting member of this invention. As shown in FIG. 3, a first (or right) connecting member 42 connects lens region 12 to temple 44, and a second (or left) connecting member 43 connects lens region 14 to temple 45. (Hereinafter, connecting member 43 will be described in detail, but it is understood that connecting member 42 will have similar structure.) Connecting member 43 has a top prong 51 and a bottom prong 52 at the forward end thereof and an extension 53 that extends rearwardly from the juncture of the top and bottom prongs 51,52, such that connecting member 43 has a general Y-shape. Temple 45 is connected to the distal end of extension 53, e.g., through a pivotal connection such as hinge assembly 47. Top and bottom prongs 51,52 have lateral grooves 53,54 in opposed inner surfaces thereof, such that edges of lens 10 are received in the lateral grooves. More specifically, an end portion of top edge 11 is engaged in lateral groove 53, and an end portion of bottom edge 13 is engaged in lateral groove 54.

Figure 9:
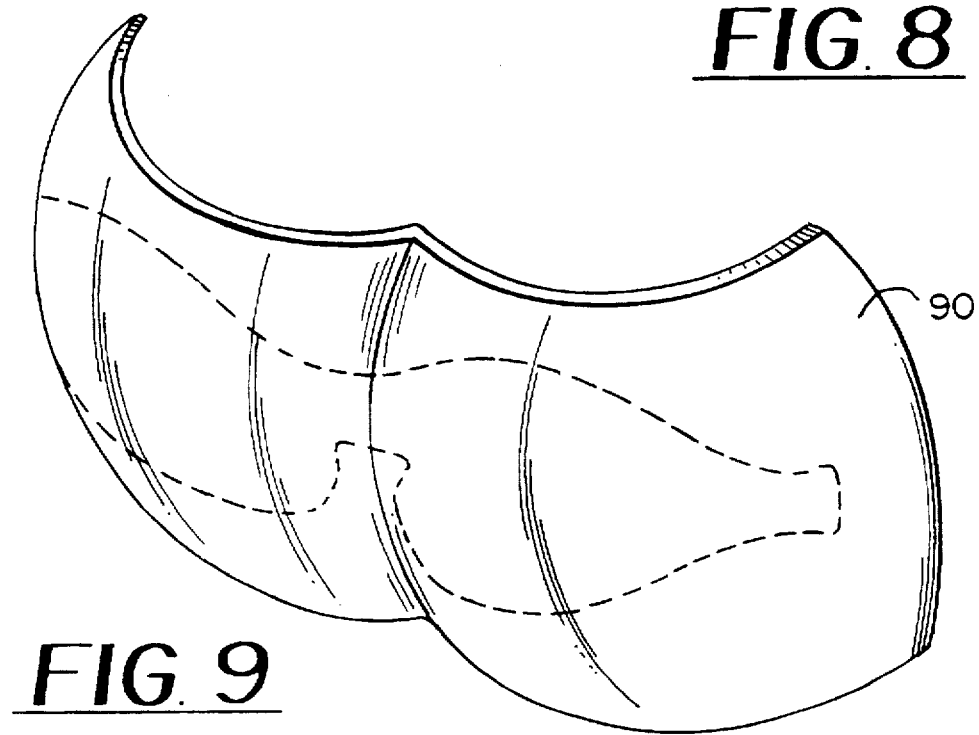
FIG. 9 is a perspective view of a lens blank, further showing the lens of FIG. 3 with dashed lines.

Preferably, lens 10 further comprises projection 40 projecting from its side, wherein projection 40 is received in opening 55 extending axially through the interior of extension 53 as a male/female connection. Projection 40 (as well as a corresponding projection on the other side of lens 10) is an integral part of lens 10, such that the projections may be cut from blank 90 with the remainder of lens 10 (FIG. 9). Accordingly, projection 40 is part of the substantially spherical portion forming surface 4. Projection 40 may include top and bottom detents 56,57, and connecting member 43 may include corresponding top opening 58 and bottom opening (not shown) for removably receiving the detents. The detents and the corresponding openings in the connecting member facilitate a snap interfit. A snap interfit provides for interchangeability of lenses, i.e., a wearer can change temples or lenses by removing and replacing connecting members 42 and 43. Preferably, the top and bottom openings are aligned to form a single passage extending vertically and transversely through extension 53. Additionally, a notch 59 may be provided in the end edge of projection 40 for engagement with a peg extending transversely in opening 55, to ensure that the projection is aligned properly once inserted in the opening of the connecting member.

Connecting member 43 may then be attached to temple 45 in a conventional manner, such as with a screw, rivet, or snap-on interfit. As shown in the figures, connecting member 43 and temple 45 are connected with a standard hinge assembly 47.

It will be appreciated that the connecting members are useful for eyewear having lenses other than the lens of the present invention. For example, the connecting members may be used on eyewear having a conventional unitary lens, and eyewear having two lenses connected by a bridge.

The connecting members may be made from a molded thermoplastic material such as those generally described above for lens 10. Alternatively, the connecting member can be made from a thermoplastic material such as polypropylene or an thermoplastic elastomer. It is preferred that the material used for the connecting members has sufficient resilience to allow the described frictional interfit with the lens.

As discussed supra, indentation 17 of lens 10 can be designed to fit directly on the nose, but it is preferred that the lens is provided with a nosepiece. A preferred nosepiece 81 is shown in FIGS. 5 to 8. This design is less obtrusive to the wearer's vision than conventional nosepieces employed with unitary lens designs, and especially less intrusive than nosepieces that wrap around a bridge between lenses. As shown best in FIG. 6, the construction of nosepiece 81 moves the bulk of its mass downwardly along the nose of the wearer and below the normal line of vision of the wearer.

The preferred nosepiece includes outwardly extending legs 82,83 and a top 89, having opposite front and rear surfaces 89' and 89", respectively (FIGS. 5 and 7), such that the nosepiece has an inverted "U" shape as viewed from its front or its rear, preferably in a keyhole configuration as shown. More particularly the top 89 and legs 82, 83 together form a central nosepiece opening 71. The junctures of top 89 and legs 82, 83 are slightly indented such that the width of opening 71 at top 89, designated in FIG. 6 as "$w_1$", is larger than the width of opening 71 at the juncture points 73 and 75, designated "$w_2$". The legs include grooves 87,88 each having groove bottom surfaces 87', 88', respectively, in the outer surfaces thereof for receiving indentation 17 in bottom edge 13 of lens 10. The rear of the legs 82,83 further include rearwardly extending wings 84,85 for sitting on the nose of a wearer. The rear surface of top 89 has an abutment face 91 above wings 84,85 and extending above the top of the nosepiece.

Accordingly, bottom edge 13 of lens 10 is received in grooves 87 and 88. Terminals 19 and 20 of bottom edge 13 (projecting inwardly in central indentation 17) mate with nosepiece 81 at a point just above the termination point of grooves 87 and 88, i.e., substantially at juncture points 73 and 75, respectively, which configuration securely retains nosepiece 81 within indentation 17 until forcibly removed therefrom. Top 89 abuts the edge at the top of indentation 17 wherein abutment face 91 abuts the back of lens 10.

As mentioned supra, nosepiece 81 sits below the field of vision of the wearer. Moreover, the design of nosepiece 81 and the complimentary portion of lens 10, indentation 17, provides for a less hazardous design than conventional unitary lenses made for receiving nose pieces. Such conventional designs require multiple inward projections on the lens to receive and hold conventional nosepieces in place. These convention projections tend to be rather pointed or sharp and can lead to injury to the nose if the nosepiece is dislodged. Conversely, nosepiece 81 fits securely on lens 10 without the need for such pointed projections as terminals 19 and 20 have a more rounded configuration and are unlikely to cause injury if nosepiece 81 is dislodged.

Nosepiece 81 is made of a suitable material to confer the proper resiliency whereby it can elastically deform for insertion or removal. Further, nosepiece 81 is made of a material which will not easily slide on the nose when moistened by perspiration. Examples of such materials include thermoplastic resins such as polypropylene or thermoplastic elastomers. Nosepiece 81 may be molded in two pieces, then joined by an adhesive or other means, along mate line 91.

Although only a few embodiments of the present invention have been specifically described above, it should be appreciated that many additions and modifications can be made without departing from the spirit and scope of this invention. Further, it is understood that the subject invention is not limited by the example or embodiments set forth above, but shall include modifications and variations that fall within the scope of the attached claims.

What is claimed is:

1. A nosepiece for a unitary lens comprising:

a) a top portion having opposite front and rear surfaces and right and left sides;

b) first and second legs each having opposite front and rear surfaces, said first and second legs extending downwardly from said right and left sides of said top portion, respectively, said first and second legs and said top portion together forming a central nosepiece opening, the junctures of said top portion and each of said legs being indented such that the width $w_1$ of said nosepiece opening at said top is larger than the width $w_2$ of said nosepiece opening adjacent said junctures;

c) first and second grooves formed in said first and second legs between said front and rear surfaces thereof, respectively, for receiving an edge of said unitary lens, said first and second grooves extending along said first and second legs, respectively, from a point below said junctures with respect to said top portion.

2. The nosepiece of claim 1, wherein said legs gradually flare outwardly with respect to each other as they extend away from said top portion.

3. The nosepiece according to claim 1, and further including first and second wing portions attached to said rear portions of said first and second legs, respectively, said wing portions being configured for resting on the nose of the wearer.

4. The nosepiece of claim 1, and further comprising an abutment face having opposite front and rear surfaces, said abutment face attached to said rear surface of said top portion and extending above said top portion in a direction opposite to said first and second legs, said front surface of said abutment face and said front surface of said top portion lying in spaced, substantially parallel planes.

5. The nosepiece of claim 4 wherein said edge of said unitary lens has opposite front and rear surfaces, and wherein said front surface of said abutment face engages said rear surface of said lens edge, and said front surface of said top portion lies substantially flush with said front surface of said lens edge, upon attaching said nosepiece to said unitary lens.

6. The nosepiece of claim 1 wherein said first and second grooves each have a substantially smooth bottom surface.

7. The nosepiece of claim 6 wherein said bottom surfaces of said first and second grooves are arcuately shaped.

* * * * *